(12) United States Patent
Kim et al.

(10) Patent No.: US 12,310,756 B2
(45) Date of Patent: May 27, 2025

(54) COMPUTER DEVICE FOR ATTENUATING MOTION ARTIFACTS IN PHOTOPLETHYSMOGRAPHY IN REAL TIME IN ORDER TO REDUCE DISTORTION ATTRIBUTABLE TO CHANGE IN DISTANCE OF SENSOR AND METHOD USING THE SAME

(71) Applicant: Korea Advanced Institute of Science and Technology, Daejeon (KR)

(72) Inventors: Chul Kim, Daejeon (KR); Sanghyun Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 524 days.

(21) Appl. No.: 17/707,722

(22) Filed: Mar. 29, 2022

(65) Prior Publication Data

US 2023/0172558 A1    Jun. 8, 2023

(30) Foreign Application Priority Data

Dec. 8, 2021    (KR) .......................... 10-2021-0174523

(51) Int. Cl.
*A61B 5/00*      (2006.01)
*A61B 5/024*     (2006.01)

(52) U.S. Cl.
CPC ........ *A61B 5/7214* (2013.01); *A61B 5/02416* (2013.01); *A61B 5/7225* (2013.01);
(Continued)

(58) Field of Classification Search
CPC . A61B 5/7214; A61B 5/02416; A61B 5/7225; A61B 5/7207; A61B 5/7228;
(Continued)

(56) References Cited

FOREIGN PATENT DOCUMENTS

KR        20160028351 A      3/2016

OTHER PUBLICATIONS

Wikipedia ("Field-programmable gate array." Wikipedia, The Free Encyclopedia. Wikipedia, The Free Encyclopedia, Aug. 2, 2021) ( Year: 2021).*

(Continued)

*Primary Examiner* — Lisa M Caputo
*Assistant Examiner* — Christian T Bryant
(74) *Attorney, Agent, or Firm* — BKRIP LLC

(57) ABSTRACT

Various embodiments provide a computer device for attenuating motion artifacts in photoplethysmography (PPG) in real time and a method using the same. The computer device obtains a primarily restored PPG AC signal from a distorted PPG signal by using an exponentially weighted moving average filter and restores the final PPG AC signal from the primarily restored PPG AC signal through block interleaving. The computer device includes an initial unit obtaining a basic period of a PPG signal from a PPG sensor in an initial state, an update unit obtaining a waveform and period of a PPG signal not having distortion from the PPG sensor in the state in which motion artifacts are not present, a compensation unit detecting the final PPG AC signal by restoring a waveform of the distorted PPG signal, and a command unit outputting the final PPG AC signal.

16 Claims, 13 Drawing Sheets

(52) U.S. Cl.
CPC ........... *A61B 5/7203* (2013.01); *A61B 5/7207* (2013.01); *A61B 5/7221* (2013.01); *A61B 5/7228* (2013.01); *A61B 5/725* (2013.01); *A61B 5/7278* (2013.01)

(58) Field of Classification Search
CPC ..... A61B 5/725; A61B 5/7203; A61B 5/7278; A61B 5/7221
See application file for complete search history.

(56) References Cited

OTHER PUBLICATIONS

Lee (Motion artifacts reduction from PPG using cyclic moving average filter. Technol Health Care. 2014;22(3):409-17. doi: 10.3233/THC-140798. PMID: 24704660.) (Year: 2014).*

Lee (The Motion Artifact Reduction from the PPG based on EWMA. Journal of Digital Convergence. 11, p. 183-190. Aug. 2013) (Year: 2013).*

Krishnan et al. ("Two-Stage Approach for Detection and Reduction of Motion Artifacts in Photoplethysmographic Data," in IEEE Transactions on Biomedical Engineering, vol. 57, No. 8, pp. 1867-1876, Aug. 2010, doi: 10.1109/TBME.2009.2039568.) (Year: 2010 ).*

The Motion Artifact Reduction from the PPG based on EWMA, The Journal of Digital Policy Management, 11(8): pp. 183-190 (Aug. 2013).

Byung S. Kim et al,, Motion Artifact Reduction in Photoplethysmography Using Independent Component Analysis, IEEE Trans. Biomed. Eng., vol. 53, No. 3, pp. 566-568 (Mar. 2006).

* cited by examiner

COMPUTER DEVICE FOR ATTENUATING MOTION ARTIFACTS IN PHOTOPLETHYSMOGRAPHY IN REAL TIME IN ORDER TO REDUCE DISTORTION ATTRIBUTABLE TO CHANGE IN DISTANCE OF SENSOR AND METHOD USING THE SAME

CROSS-REFERENCES TO RELATED APPLICATIONS

This application is based on and claims priority under 35 U.S.C. 119 to Korean Patent Application No. 10-2021-0174523, filed on Dec. 8, 2021 in the Korean intellectual property office, the disclosure of which is herein incorporated by reference in its entirety.

TECHNICAL FIELD

Various embodiments relate to a computer device for attenuating motion artifacts in photoplethysmography in real time in order to reduce distortion attributable to a change in the distance of a sensor and a method using the same.

BACKGROUND OF THE DISCLOSURE

Photoplethysmography (PPG) is a technology for noninvasively measuring a change in the blood volume of a microvessel of a tissue by using light. A PPG signal is defined as an alternating component (AC) having pulsation and a direct component (DC) that is rarely changed. The spectrum of the PPG signal is known to be 0.5 to 4 Hz. The AC occupies about 1% of the entire PPG signal and derived by a change in the volume of a blood vessel synchronized with a heartbeat. The DC is derived by the transmission or reflection of a sympathetic nervous system, a tissue, and a bone under the skin.

The reason why such PPG has recently been in the spotlight lies in the easiness of measurement and various pieces of bio information which may be extracted through measurement. The PPG is presented as an important alternative of an electrocardiogram (ECG) for analyzing electrical activities of the heart by using electrodes attached to the skin because the PPG can be used for measurement at a single point, such as a wrist, the end of a finger, and a thigh. Furthermore, the PPG is frequently used in devices for health care because useful information, such as an endothelium function, a cardiac output, an autonomous function, arterial aging, and cardiac variability, can be obtained through obtained PPG.

Despite the presented advantages, the PPG has a disadvantage in that it is very vulnerable to motion artifacts derived by a change in the distance of a sensor in terms of a photoelectric measuring instrument. In order to solve such a disadvantage, the existing compensation algorithms have adopted compensation methods, such as the analysis of independent components, adaptive noise cancellation, and Fourier series analysis which may be applied to two independent variables, based on the assumption that the PPG and motion artifacts are statistically independent. However, the corresponding algorithms tend to have low restoration accuracy of a PPG signal as the strength of a motion is increased. Accordingly, an opinion that the PPG signal and the motion artifacts do not have an independent relation has been presented. The corresponding algorithms based on the assumption of the independent relation can perform compensations to some extent because frequency bands of motion artifacts and PPG are overlapped, but have a problem in that they have low accuracy as a motion becomes fast or a ratio of non-independent motion artifacts is increased.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Various embodiments propose a motion artifact compensation algorithm based on a non-independent relation in order to overcome the accuracy limit of the existing motion artifact compensation algorithm in which photoplethysmography (PPG) and motion artifacts are assumed to have a statistical independent relation.

The existing compensation algorithm chiefly uses methods, such as the analysis of independent components and Fourier series analysis based on statistical independence, but has an accuracy limit. The possibility of non-independent relation between PPG of compensations and motion artifacts has recently been presented. Various embodiments are intended to increase the accuracy of restoration based on gain variation modeling based on the non-independent relation.

Furthermore, various embodiments are intended to enable the restoration of a PPG signal in real time under a daily life environment by reducing distortion derived due to a motion through an algorithm.

In various embodiments, a computer device includes a photoplethysmography (PPG) sensor configured to measure PPG, and a processor connected to the PPG sensor and configured to restore a final PPG AC signal by compensating for motion artifacts of a distorted PPG signal from the PPG sensor. The processor is configured to obtain a primarily restored PPG AC signal from the distorted PPG signal by using an exponentially weighted moving average filter and to restore the final PPG AC signal from the primarily restored PPG AC signal through block interleaving.

In various embodiments, a method of a computer device includes receiving a distorted photoplethysmography (PPG) signal from a PPG sensor measuring PPG, and restoring a final PPG AC signal by compensating for motion artifacts of the distorted PPG signal. Restoring the final PPG AC signal includes obtaining a primarily restored PPG AC signal from the distorted PPG signal by using an exponentially weighted moving average filter, and restoring the final PPG AC signal from the primarily restored PPG AC signal through block interleaving.

In various embodiments, one or more programs for executing, in a computer device, a method of restoring a final photoplethysmography (PPG) AC signal by compensating for motion artifacts of a distorted PPG signal from a PPG sensor measuring PPG are recorded on a non-transitory computer-readable recording medium. The method includes obtaining a primarily restored PPG AC signal from the distorted PPG signal by using an exponentially weighted moving average filter, and restoring the final PPG AC signal from the primarily restored PPG AC signal through block interleaving.

According to various embodiments, it is expected that data restoration efficiency can be increased through a method in which a non-independent relation between a PPG signal and motion artifacts is considered with a difference from most of the existing algorithms for compensations based on the independence of a PPG signal and motion artifacts. Accordingly, it is expected that the computer device according to various embodiments may be mounted on various products using PPG sensors and can contribute to the improvement of data reliability under a daily life environment.

Accordingly, various embodiments may be used to obtain accurate data of a PPG sensor under a motion artifacts environment and may be used for the real-time analysis of user bio information under a daily life environment. Furthermore, various embodiments may be widely applied to any product through the design and fabrication of an ultra-small chip based on a corresponding algorithm code in the future in a way to additionally mount an algorithm without competing with the existing health-monitoring products using the PPG sensor. Accordingly, it is expected that technical competitiveness can be secured by improving efficiency in obtaining accurate bio information through the restoration of a signal under a motion environment.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the disclosure.

Hereinafter, various embodiments of this document are described with reference to the accompanying drawings.

Figure 1:
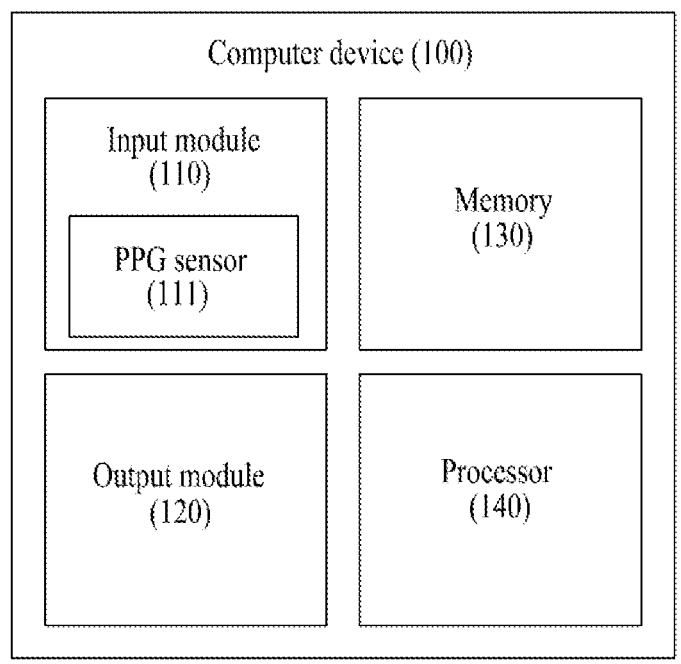
FIG. 1 is a diagram illustrating a configuration of a computer device according to various embodiments.
Figure 2:
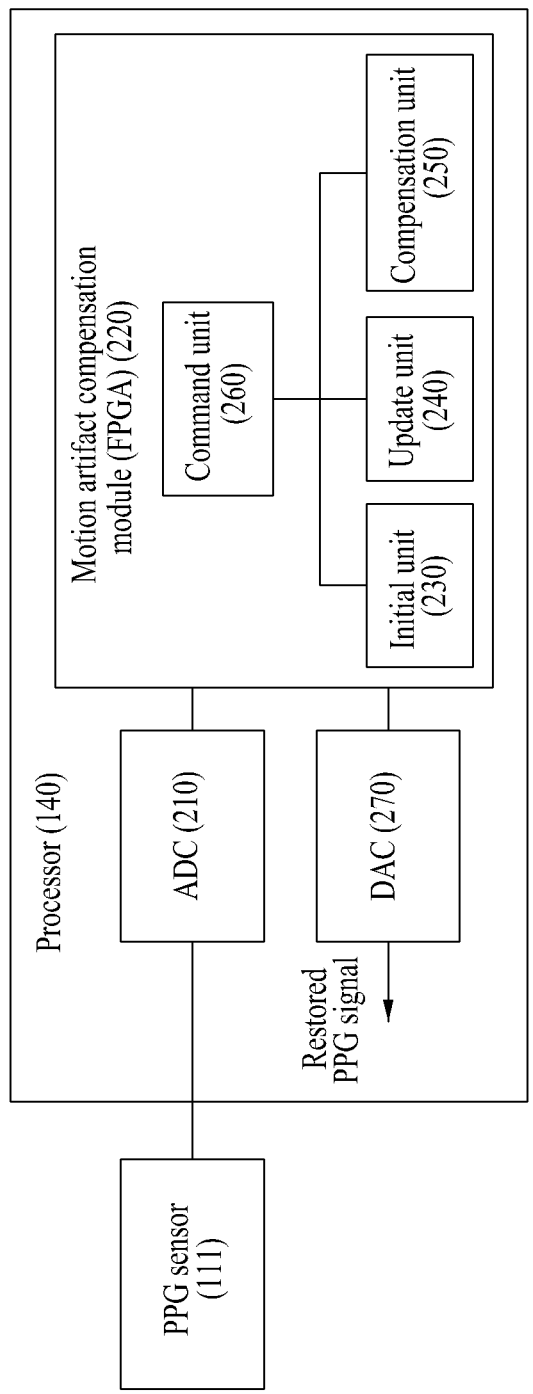
FIG. 2 is a diagram illustrating an internal configuration of a processor in FIG. 1.
Figure 3A:
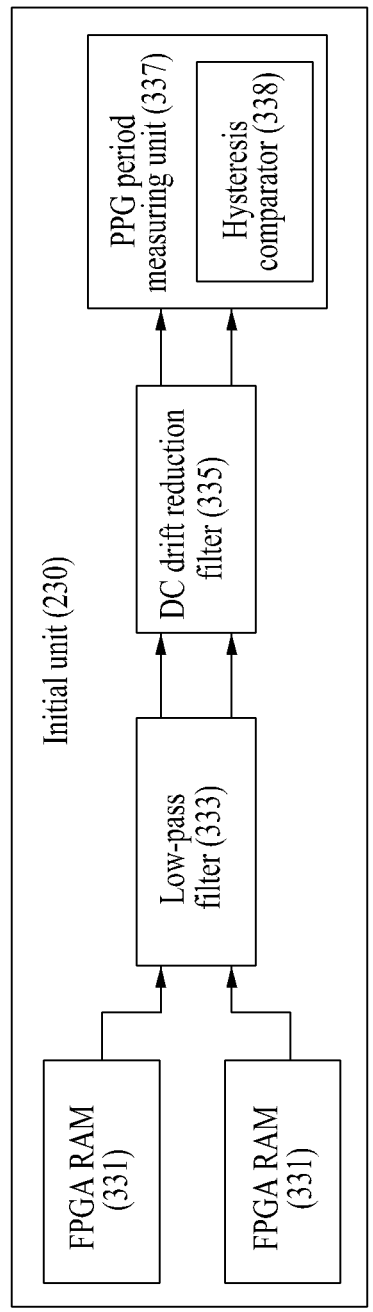
FIG. 3A is a diagram illustrating a detailed configuration of an initial unit in FIG. 2.
Figure 3B:
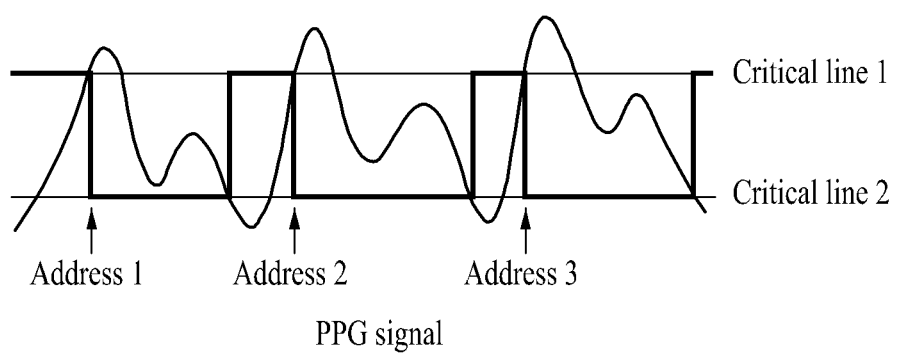
FIG. 3B is a diagram for describing an operation algorithm of the initial unit in FIG. 2.
Figure 4:
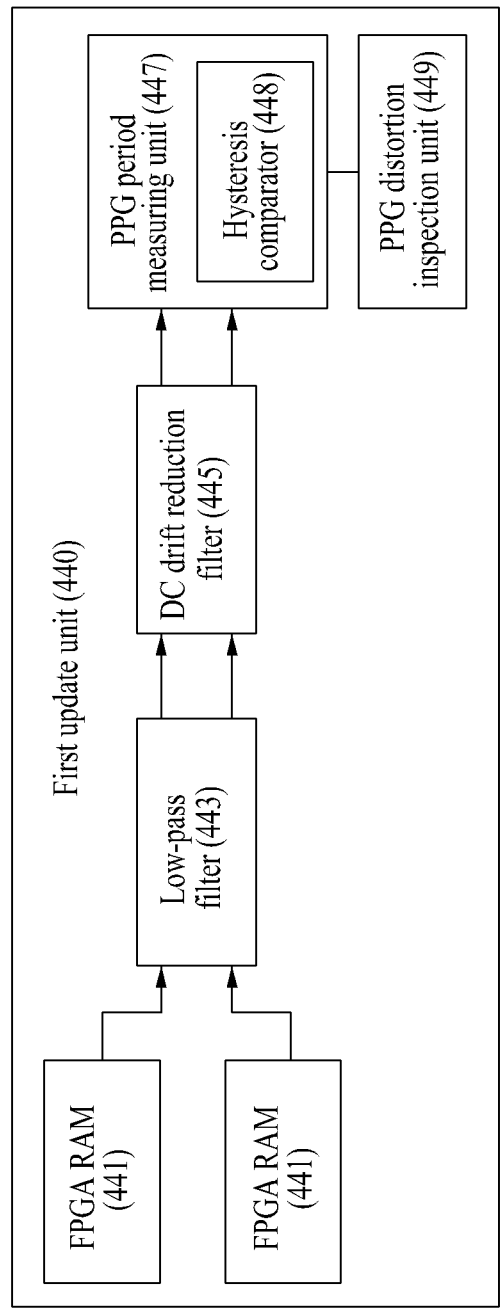
FIG. 4 is a diagram illustrating a detailed configuration of a first update unit within an update unit in FIG. 2.
Figure 5A:
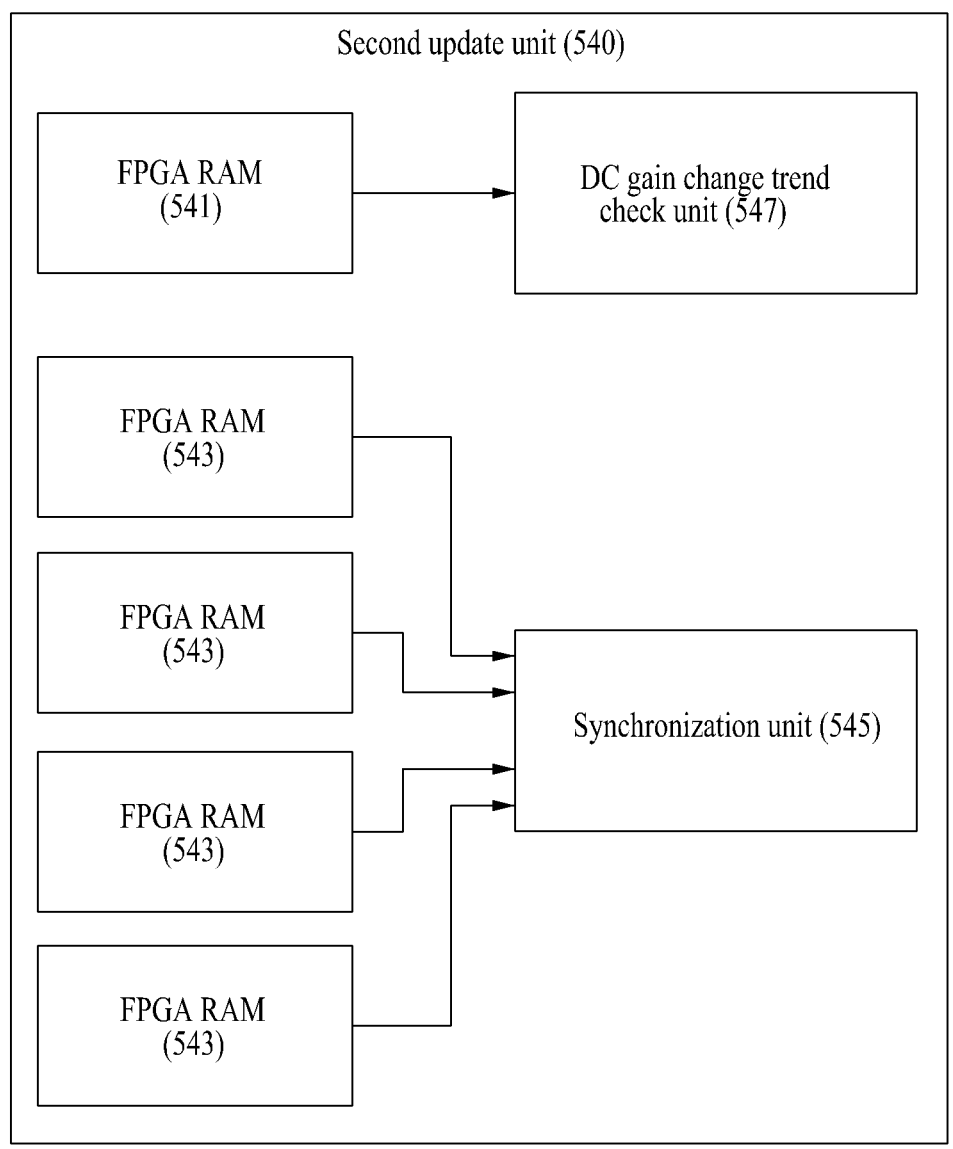
FIG. 5A is a diagram illustrating a detailed configuration of a second update unit within the update unit in FIG. 2.
Figure 5B:
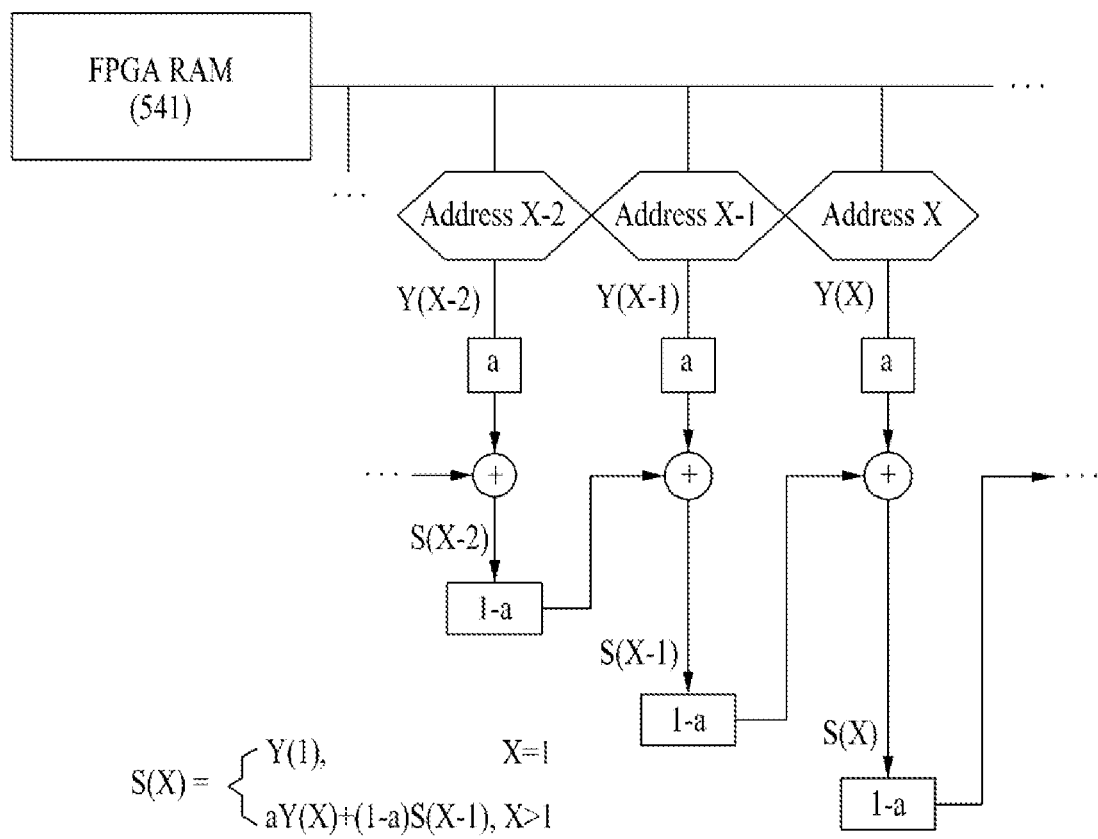
FIGS. 5B and 5C are diagrams for describing an operation algorithm of the update unit in FIG. 2.
Figure 5C:
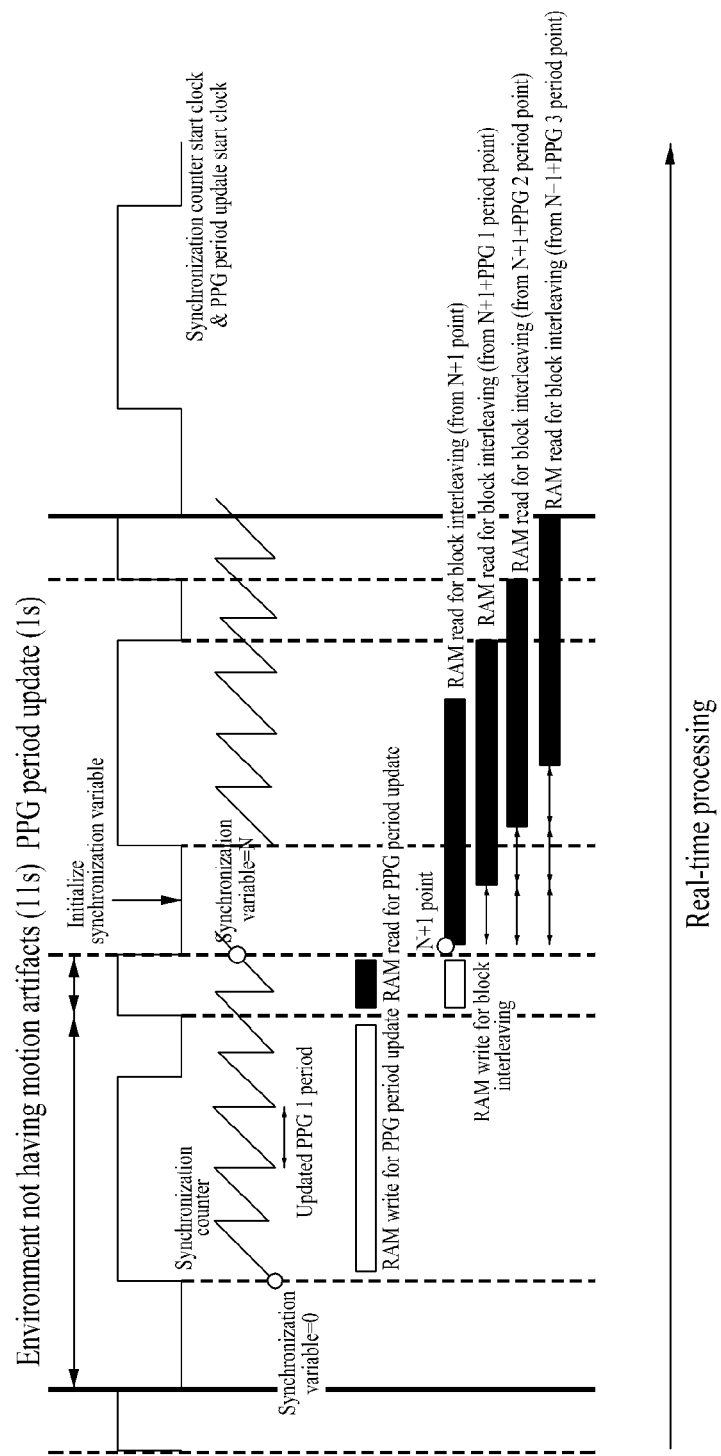
Figure 6A:
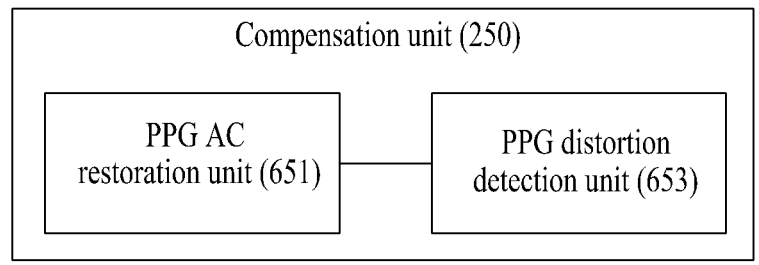
FIG. 6A is a diagram illustrating a detailed configuration of a compensation unit in FIG. 2.
Figure 6B:
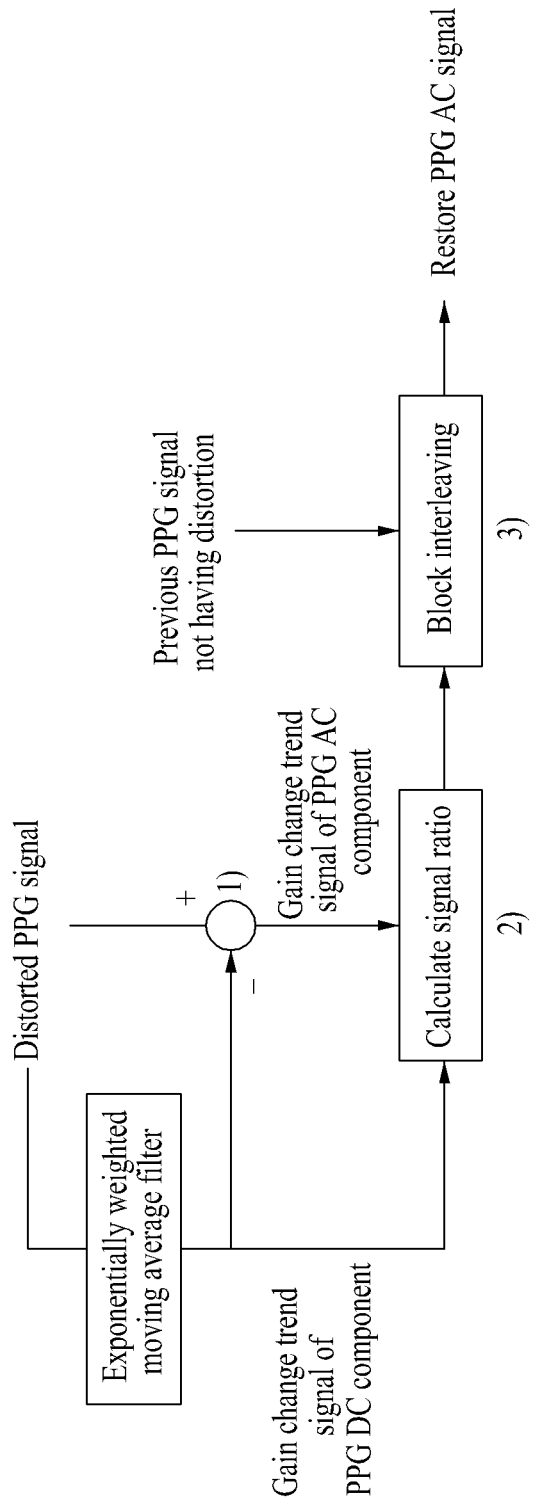
FIGS. 6B and 6C are diagrams for describing an operation algorithm of the compensation unit in FIG. 2.
Figure 6C:
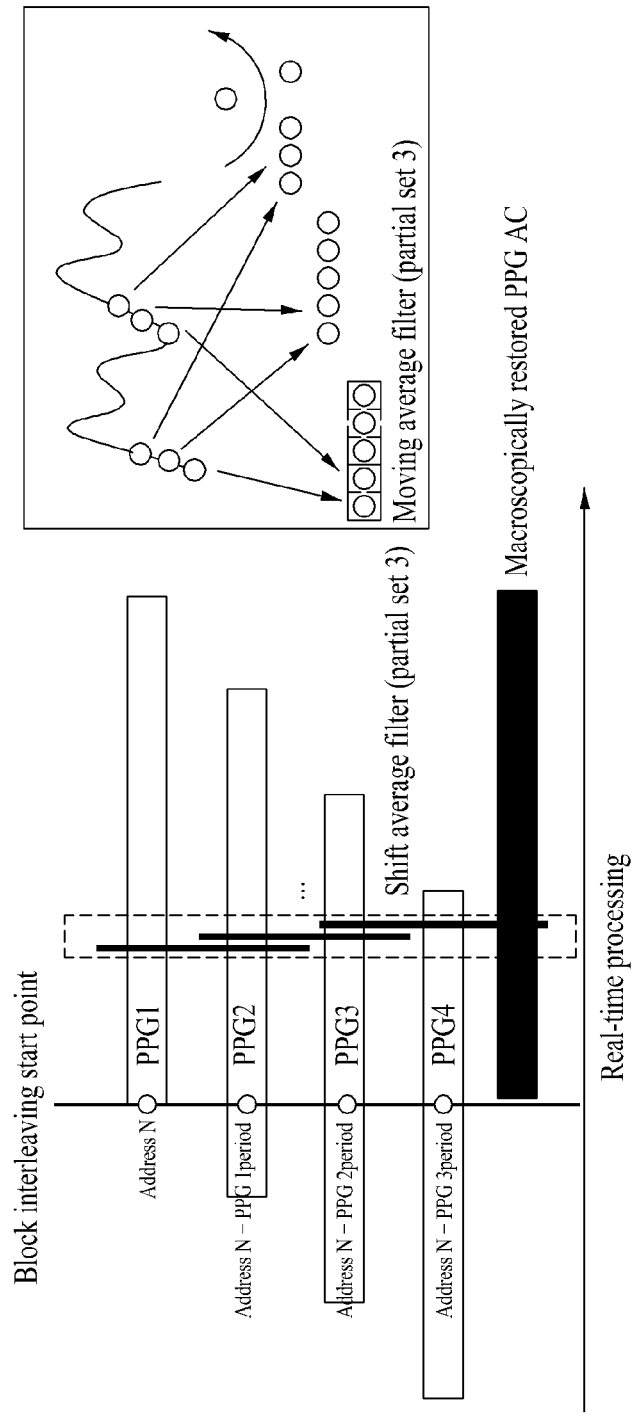
Figure 7:
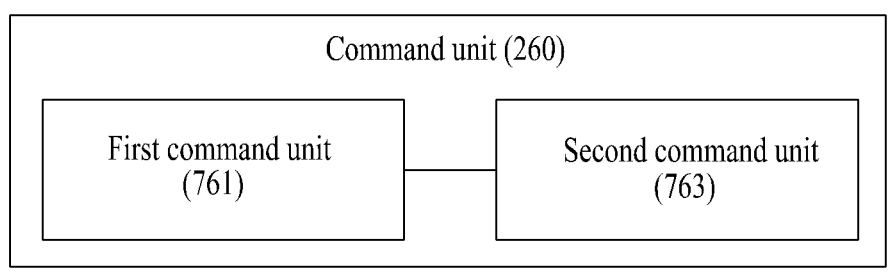
FIG. 7 is a diagram illustrating a detailed configuration of a command unit in FIG. 2.

FIG. 1 is a diagram illustrating a configuration of a computer device 100 according to various embodiments. FIG. 2 is a diagram illustrating an internal configuration of a processor 140 in FIG. 1. FIG. 3A is a diagram illustrating a detailed configuration of an initial unit 230 in FIG. 2. FIG. 3B is a diagram for describing an operation algorithm of the initial unit 230 in FIG. 2. FIG. 4 is a diagram illustrating a detailed configuration of a first update unit 440 within an update unit 240 in FIG. 2. FIG. 5A is a diagram illustrating a detailed configuration of a second update unit 540 within the update unit 240 in FIG. 2. FIGS. 5B and 5C are diagrams for describing an operation algorithm of the update unit 240 in FIG. 2. FIG. 6A is a diagram illustrating a detailed configuration of a compensation unit 250 in FIG. 2. FIGS. 6B and 6C are diagrams for describing an operation algorithm of the compensation unit 250 in FIG. 2. FIG. 7 is a diagram illustrating a detailed configuration of a command unit 260 in FIG. 2.

Referring to FIG. 1, the computer device 100 includes at least one of an input module 110, an output module 120, a memory 130, or a processor 140. In an embodiment, at least one of the components of the computer device 100 may be omitted, and at least one other component may be added to the computer device 100. In an embodiment, at least two of the components of the computer device 100 may be implemented as a single integrated circuit.

The input module 110 receives a signal to be used for at least one component of the computer device 100. The input module 110 includes at least one of an input device configured to enable a user to directly input a signal to the computer device 100, a sensor device configured to generate a signal by sensing a surrounding change, or a reception device configured to receive a signal from an external device. For example, the input device includes at least one of a microphone, a mouse or a keyboard. In an embodiment, the input device includes at least one of touch circuitry configured to detect a touch or a sensor circuit configured to measure the intensity of a force generated by a touch. In this case, the input module 110 includes a PPG sensor 111.

The output module 120 outputs information to the outside of the computer device 100. The output module 120 includes at least one of a display device configured to visually output information, an audio output device capable of outputting information in the form of an audio signal, or a transmission device capable of wirelessly transmitting information. For example, the display device includes at least one of a display, a hologram device or a projector. For example, the display device may be assembled with at least one of the touch circuit or sensor circuit of the input module 110, and thus may be implemented as a touch screen. For example, the audio output module includes at least one of a speaker or a receiver.

According to some embodiments, the reception device and the transmission device may be implemented as a communication module. The communication module performs communication with an external device in the computer device 100. The communication module establishes a communication channel between the computer device 100 and the external device, and performs communication with the external device through the communication channel. In this case, the external device includes at least one of a vehicle, a satellite, a base station, a server or another computer system. The communication module includes at least one of a wired communication module or a wireless communication module. The wired communication module is connected to the external device in a wired way, and communicates with the external device in a wired way. The wireless communication module includes at least one of a short-distance communication module or a long-distance communication module. The short-distance communication module communicates with the external device using the short-distance communication method. For example, the short-distance communication method includes at least one of Bluetooth, WiFi direct, or infrared data association (IrDA). The long-distance communication module communicates with the external device using the long-distance communication method. In this case, the long-distance communication module communicates with the external device over a network. For example, the network includes at least one of a cellular network, the Internet, or a computer network, such as a local area network (LAN) or a wide area network (WAN).

The memory 130 stores various data used by at least one component of the computer device 100. For example, the memory 130 includes at least one of a volatile memory or a nonvolatile memory. The data includes at least one program and input data or output data related thereto. The program may be stored in the memory 130 as software including at least one instruction, and includes at least one of an operating system, middleware, or an application.

The processor 140 controls at least one component of the computer device 100 by executing a program of the memory 130. Accordingly, the processor 140 performs data processing or an operation. In this case, the processor 140 executes an instruction stored in the memory 130.

Various embodiments propose a motion artifact compensation algorithm based on a non-independent relation between PPG and motion artifacts through a compensation algorithm based on gain variation modeling. To this end, as illustrated in FIG. 2, the processor 140 includes an analog-digital converter (ADC) 210, a motion artifact compensation module 220, and a digital-analog converter (DAC) 270.

The ADC 210 converts, into a digital signal, an analog signal of a PPG signal from the PPG sensor 111. In this case, the PPG signal from the PPG sensor 111 has been distorted by motion artifacts. The motion artifact compensation module 220 is implemented as a field programmable gate array (FPGA) and has a motion artifact compensation algorithm installed therein. To this end, the motion artifact compensation algorithm is implemented in the form of a code which may be installed in the FPGA. Accordingly, the motion artifact compensation module 220 can compensate for motion artifacts in real time with respect to the PPG signal from the PPG sensor 111. The DAC 270 converts, into an analog signal, the digital signal of the PPG signal from the motion artifact compensation module 220. In this case, motion artifacts of the PPG signal from the motion artifact compensation module 220 have been compensated for.

Specifically, the PPG signal distorted by motion artifacts is represented like [Equation 1] through gain variation modeling according to various embodiments. The motion artifact compensation module 220 has an object of obtaining a "finally restored PPG AC", and uses that a PPG DC occupies almost all PPG signal components. The motion artifact compensation module 220 macroscopically restores a PPG AC signal by using an algorithm represented like [Equation 2] using an exponentially weighted moving average filter in order to cancel a PPG DC whose amount of gain has changed, which occupies the largest part of a PPG signal distorted by motion artifacts. Thereafter, the motion artifact compensation module 220 microscopically restores a PPG AC signal by using an algorithm represented like [Equation 3] using block interleaving.

$$\text{Distorted } PPG \text{ signal} = (\text{gain variation 1}) \times PPG\ DC + (\text{gain variation 2}) \times PPG\ AC \quad \text{[Equation 1]}$$

$$\text{Macroscopically restored } PPG\ AC = \text{extra } PPG\ DC + (\text{gain variation 2}) \times PPG\ AC \quad \text{Equation [2]}$$

$$\text{Finally restored } PPG \text{ signal} = \text{microscopically restored } PPG\ AC \quad \text{[Equation 3]}$$

The motion artifact compensation module 220 basically includes four components, and includes an initial unit 230 for obtaining a basic period of a PPG signal of a user, an update unit 240 for newly recording a waveform and period of a PPG signal whenever motion artifacts are not present, a compensation unit 250 for restoring a waveform of a PPG signal when motion artifacts occur, and a command unit 260 for executing each of the initial unit 230, the update unit 240 and the compensation unit 250 based on a condition.

The initial unit 230 includes components illustrated in FIG. 3A. That is, the initial unit 230 includes (1) two FPGA RAMs 331 for simultaneously storing values of PPG signals received from the PPG sensor 111 and invoking values with different delay, (2) a digital low-pass filter 333 for a cancelling other noise, (3) a DC drift reduction filter 335 for a PPG signal in the state in which motion artifacts are not present, and (4) a PPG period measuring unit 337 including a hysteresis comparator 338.

A driving algorithm of the initial unit 230 is as follow. PPG signals stored in the two FPGA RAMs 331, respectively, are read with given delay, and are then delivered to the PPG period measuring unit 337 via the low-pass filter 333 and the DC drift reduction filter 335. The delivered two PPG signals are used to change a value of a critical line of the hysteresis comparator 338 from a high value to a low value and from a low value to a high value. As illustrated in FIG. 3B, the PPG period measuring unit 337 presets a high value (critical line 1) and low value (critical line 2) of the critical line of the hysteresis comparator 338 by using one valley, a peak, and a DC value among the PPG signals passing through the low-pass filter 333 and the DC drift reduction filter 335. Thereafter, the PPG period measuring unit 337 checks addresses (address 1, address 2, . . . , address 5) of a RAM five times when a value of the critical line of the hysteresis comparator 338 changes from a high value to a low value. Accordingly, the PPG period measuring unit 337 obtains a basic period of the PPG signal by calculating an average of corresponding addresses.

Components of the update unit 240 are basically divided into two, that is, a first update unit 440 for newly recording a waveform and period of a PPG signal in the state in which motion artifacts are not present and a second update unit 540 for previously calculating information necessary to restore a PPG signal in real time and delivering the calculated information to the compensation unit 250.

As illustrated in FIG. 4, the first update unit 440 of the update unit 240 includes (5) two FPGA RAMs 441 for simultaneously storing values of PPG signals received from the PPG sensor 111 and invoking values with different delay, (6) a digital low-pass filter 443 for cancelling other noise, (7) a DC drift reduction filter 445 for a PPG signal in the state in which motion artifacts are not present, (8) a PPG period measuring unit 447 including a hysteresis comparator 448, and (9) a PPG distortion inspection unit 449 for inspecting whether a PPG signal has been distorted.

The FPGA RAMs 441, low-pass filter 443, DC drift reduction filter 445 and PPG period measuring unit 447 of the update unit 240 are configured similar to the FPGA RAMs 331 of the initial unit 230, that is, the low-pass filter 333, the DC drift reduction filter 335, and the PPG period measuring unit 337. In this case, unlike the PPG period measuring unit 337 of the initial unit 230, the PPG period measuring unit 447 of the update unit 240 are driven only when motion artifacts is not present for a specific time or more necessary for an update, and are processed at a speed several times higher than the speed of the PPG period measuring unit 337 of the initial unit 230 for an real-time update. When a value of a PPG signal is greater than or less than a designated reference value, the PPG distortion inspection unit 449 stops the PPG period measuring unit 447 and operates a restoration algorithm of the compensation unit 250.

As illustrated in FIG. 5A, the second update unit 540 of the update unit 240 includes (10) one FPGA RAM 541 for storing a signal necessary for the motion artifact restoration algorithm using the exponentially weighted moving average filter, (11) four FPGA RAMs 543 for storing a signal necessary for the restoration algorithm using a the block interleaving algorithm, (12) a synchronization unit 545 for synchronizing PPG signals stored in the FPGA RAMs 543 and a real-time PPG signal, and (13) a DC gain change trend check unit 547.

The DC gain change trend check unit 547 obtains a DC gain change trend of a distorted PPG signal by using the FPGA RAM 541 and delivers the DC gain change trend to the compensation unit 250, based on an operation algorithm such as that illustrated in FIG. 5B. Each of the FPGA RAMs 543 invokes a value with different delay for each of the FPGA RAM 543 by a designated period of the same PPG signal stored in the four FPGA RAMs 543 when motion artifacts are not present for a given time, and delivers the value to the compensation unit 250. In this case, each delay is calculated by the PPG period measuring unit 447 and the synchronization unit 545, and is the same as the sum of "0 multiple, 1 multiple, 2 multiple, or 3 multiple" and "synchronization variable+1" of a period of a PPG signal based on an operation algorithm such as that illustrated in FIG. 5C.

As illustrated in FIG. 6A, components of the compensation unit 250 include (14) a PPG AC restoration unit 651 for restoring an AC of a PPG signal having distortion by using signals received from the FPGA RAM 541 and FPGA RAMs 543 of the update unit 240, and (15) a PPG distortion detection unit 653 for detecting the distortion of a PPG signal.

An operation algorithm of the PPG AC restoration unit 651 is illustrated in FIG. 6B. Specifically, 1) the PPG AC restoration unit 651 calculates a difference between distorted PPG signals received from the FPGA RAMs 441 of the first update unit 440 and a DC gain change trend signal of a distorted PPG signal received from the FPGA RAM 541 of the second update unit 540. The obtained signal is named a "signal 1", and includes an extra PPG DC signal and a distorted PPG AC signal. 2) the PPG AC restoration unit 651 calculates a ratio of the "signal 1" and a signal received from the FPGA RAM 541 of the second update unit 540 by using that a gain variation of a PPG DC and a gain variation of a PPG AC are similar due to gain variation modeling. The obtained signal is named a "signal 2", and is a macroscopically restored PPG AC. 3) the PPG AC restoration unit 651 obtains a microscopically restored PPG AC signal through the block interleaving algorithm by using the "signal 2" and a signal received from the FPGA RAMs 543 of the second update unit 540.

In this case, an operating method of the block interleaving algorithm is illustrated in FIG. 6C. Specifically, the block interleaving algorithm groups signals received from the FPGA RAMs 543 of the second update unit 540 with different pieces of delay every three signals, and sequentially calculates averages of the signals. An average of the last three signals is a microscopically restored final PPG AC signal. The processes are individually performed on one address. Accordingly, the restoration of the PPG signal is completed, and data and a waveform deviating from the quasi-periodicity of PPG are cancelled and restored, respectively.

The PPG distortion detection unit 653 receives information on whether a signal has been distorted from the PPG distortion inspection unit 449 of the first update unit 440, and operates the PPG AC restoration unit 651 for a specific time when distortion is detected. Thereafter, when the distortion of a signal is not detected for a specific time, the PPG distortion detection unit 653 stops the operation of the PPG AC restoration unit 651.

As illustrated in FIG. 7, components of the command unit 260 include (16) a first command unit 761 having an algorithm for transmitting a designated value to the DAC 270, and (17) a second command unit 763 including a finite-state machine algorithm having the initial unit 230, the update unit 240, and the compensation unit 250 as state variables.

An initial state is the initial unit 230, and is automatically changed into the update unit 240 when the PPG period measuring unit 337 of the initial unit 230 is completed. Thereafter, when the distortion of a PPG signal is detected by the PPG distortion inspection unit 449 of the update unit 240, the state of the compensation unit 250 is maintained or the initial state is changed into the compensation unit 250. A final signal obtained from the PPG AC restoration unit 651 of the compensation unit 250 is assigned to the first command unit 761. When the distortion of a PPG signal is not detected by the PPG distortion inspection unit 449 of the update unit 240, the state of the update unit 240 is maintained or the initial state is changed into the update unit 240. A signal having small delay among signals obtained from the FPGA RAMs 441 of the update unit 240 is assigned to the first command unit 761.

Figure 8:
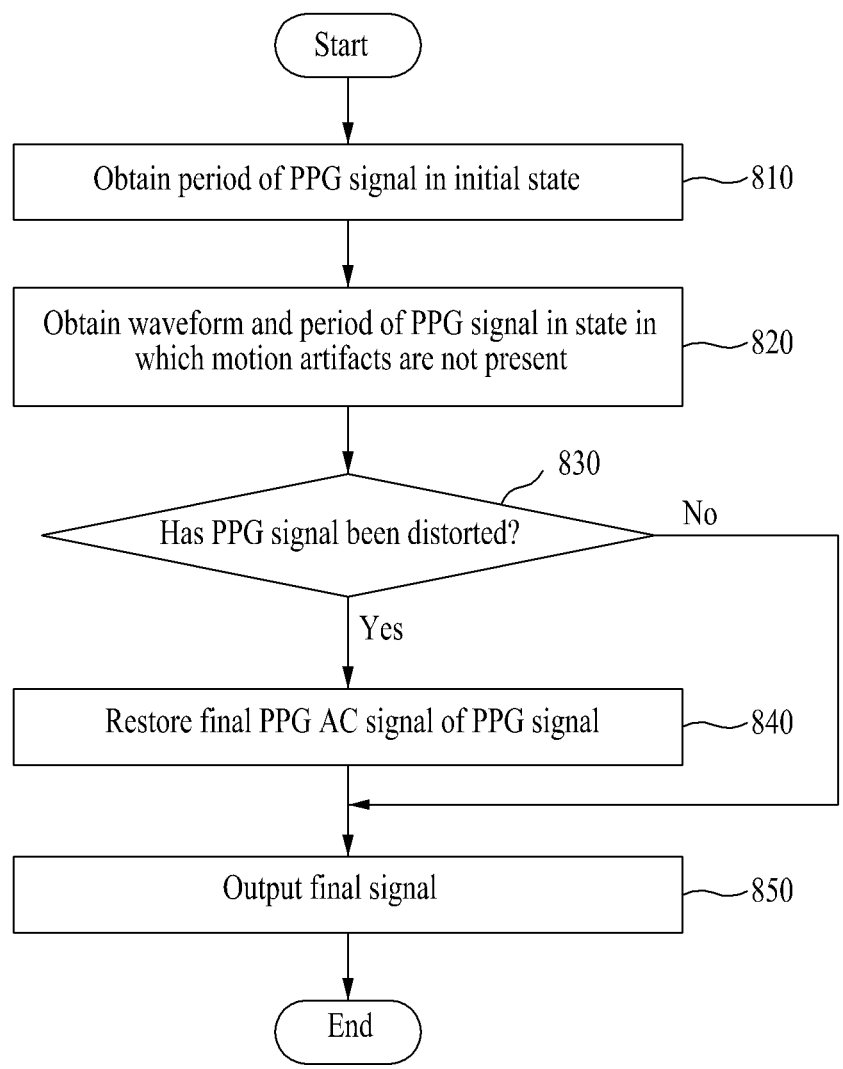
FIG. 8 is a diagram illustrating a method of the computer device according to various embodiments.

FIG. 8 is a diagram illustrating a method of the computer device 100 according to various embodiments.

Referring to FIG. 8, in step 810, the motion artifact compensation module 220 obtains a basic period of a PPG signal in the initial state. Specifically, the initial unit 230 obtains the basic period of the PPG signal in the initial state.

Next, in step 820, the motion artifact compensation module 220 obtains a waveform and period of the PPG signal in the state in which motion artifacts are not present. Specifically, the PPG period measuring unit 447 of the update unit 240 obtains the waveform and period of the PPG signal in the state in which motion artifacts are not present.

Next, in step 830, the motion artifact compensation module 220 inspects whether the PPG signal has been distorted. Specifically, the PPG distortion inspection unit 449 of the update unit 240 inspects whether the PPG signal has been distorted.

When distortion is detected in step 830, in step 840, the motion artifact compensation module 220 restores the final PPG AC signal of the distorted PPG signal. In this case, when distortion is detected, the PPG distortion inspection unit 449 stops the PPG period measuring unit 447 and operates the compensation unit 250. Furthermore, the update unit 240 detects a DC gain change trend of the distorted PPG signal and delivers the DC gain change trend to the compensation unit 250. Accordingly, the compensation unit 250 restores a waveform of the distorted PPG signal and detects the final PPG AC signal. Specifically, the compensation unit 250 obtains a primarily restored PPG AC signal from a difference between the distorted PPG signal and the DC gain change trend by using the exponentially weighted moving average filter. Thereafter, the compensation unit 250 detects the final PPG AC signal from the primarily restored PPG signal and a PPG signal not having distortion through block interleaving, and provides the final PPG AC signal to the command unit 260.

Next, in step 850, the motion artifact compensation module 220 outputs the final PPG AC signal as the final signal. Specifically, the command unit 260 outputs the final signal to the DAC 270.

When distortion is not detected in step 830, the motion artifact compensation module 220 outputs, as the final signal, the PPG signal not having distortion. Specifically, when distortion is not detected, the update unit 240 provides the command unit 260 with the PPG signal not having distortion. Accordingly, the command unit 260 outputs the final signal to the DAC 270.

It is expected that various embodiments can increase data restoration efficiency through a method in which a non-independent relation between a PPG signal and motion artifacts is considered with a difference from most of the existing algorithms that perform compensation based on independence between a PPG signal and motion artifacts. It is expected that various embodiments may contribute to the improvement of data reliability under a daily life environment by being mounted on various products using the PPG sensor 111 in the future.

Accordingly, various embodiments may be used to obtain accurate data of the PPG sensor 111 under a motion artifact environment and thus may be applied to the real-time analysis of user bio information under a daily life environment. Furthermore, various embodiments may be widely applied to any product through the design and fabrication of an ultra-small chip based on a corresponding algorithm code in the future in a way to additionally mount an algorithm without competing with the existing health monitoring products using the PPG sensor 111. Accordingly, it is expected that technical competitiveness can be secured by improving efficiency in obtaining accurate bio information through the restoration of a signal under a motion environment.

As health becomes important, the needs for health products are increased. The PPG sensor 111 has been in the spotlight because a signal can be easily obtained through the PPG sensor due to the simplification of measuring equipment and the number of kinds of body information which may be obtained through an obtained signal is many. Accordingly, it is expected that customer needs for a product using the PPG sensor 111 continue to be increased. It seems that a method capable of compensating for the frequent distortion of a signal attributable to a motion, that is, a fatal disadvantage of the PPG sensor 111, will be required and expected. It is expected that such a demand will be satisfied through the algorithms according to various embodiments.

It is expected that if the algorithm according to various embodiments is applied, performance of a medical device using the diagnosis of sleep apnea or a health monitoring product for obtaining personal bio information can be improved and that market competitiveness will be secured. Furthermore, it is expected that in a current global COVID-19 pandemic situation, the algorithms according to various embodiments will be applied to the early diagnosis of COVID-19 by detecting Silent Hypoxia using the monitoring of an oxygen saturation.

It is expected that the algorithm according to various embodiments has been fabricated as a code for an FPGA and may be easily mounted on overall small-sized health monitoring products in the current market through the design and fabrication of an ultra-small chip through the corresponding code in the future. Furthermore, it is expected that various embodiments may have a difference by restoring a PPG signal by using a method different from most of the existing algorithms. Furthermore, the algorithm according to various embodiments can be freely modified, supplemented or improved through coding and may be immediately performed. This means that the algorithm according to various embodiments may be flexibly applied to a changing market trend and may be applied to various market products that require the restoration of a distorted PPG signal through a chip design that implement the algorithm. Today an interest in health care products tends to increase. Accordingly, it is expected that the market in the proposed algorithm will be used is also widened.

Various embodiments provide the computer device 100 for attenuating motion artifacts in photoplethysmography in real time in order to reduce distortion attributable to a change in the distance of a sensor and a method using the same.

The computer device 100 according to various embodiments includes the photoplethysmography (PPG) sensor 111 configured to measure PPG and the processor 140 connected to the PPG sensor 111 and configured to restore the final PPG AC signal by compensating for motion artifacts of a distorted PPG signal from the PPG sensor 111.

According to various embodiments, the processor 140 is configured to obtain a primarily restored PPG AC signal from the distorted PPG signal by using an exponentially weighted moving average filter and to restore the final PPG AC signal from the primarily restored PPG AC signal through block interleaving.

According to various embodiments, the processor 140 includes an initial unit 230 configured to obtain a basic period of a PPG signal from the PPG sensor 111 in an initial state, an update unit 240 configured to obtain a waveform and period of a PPG signal not having distortion from the PPG sensor in the state in which motion artifacts are not present, the compensation unit 250 configured to detect the final PPG AC signal by restoring a waveform of the distorted PPG signal, and the command unit 260 configured to output the final PPG AC signal.

According to various embodiments, the update unit 240 is configured to detect a DC gain change trend of the distorted PPG signal.

According to various embodiments, the compensation unit 250 is configured to obtain the primarily restored PPG AC signal from a difference between the distorted PPG signal and the DC gain change trend by using the exponentially weighted moving average filter.

According to various embodiments, the compensation unit 250 is configured to detect the final PPG AC signal from the primarily restored PPG signal and the PPG signal not having distortion through the block interleaving and to provide the final PPG AC signal to the command unit 260.

According to various embodiments, the update unit 240 includes the PPG period measuring unit 447 configured to obtain the waveform and period of the PPG signal not having distortion from the PPG sensor, and the PPG distortion inspection unit 449 configured to inspect whether the PPG signal from the PPG sensor 111 has been distorted and to stop the PPG period measuring unit 447 and operate the compensation unit 250 when the distortion is detected.

According to various embodiments, the update unit 240 is configured to provide the command unit 260 with the PPG signal not having distortion when the distortion is not detected.

According to various embodiments, the command unit 260 is configured to output the PPG signal not having distortion.

According to various embodiments, the processor 140 includes a field programmable gate array (FPGA). The initial unit 230, the update unit 240, the compensation unit

250, and the command unit 260 are implemented in the form of a code installable in the FPGA.

A method of the computer device 100 according to various embodiments includes a step of receiving a distorted PPG signal from the PPG sensor 111 measuring photoplethysmography and a step of restoring the final PPG AC signal by compensating for motion artifacts of the distorted PPG signal.

According to various embodiments, the step of restoring the final PPG AC signal is configured to obtain a primarily restored PPG AC signal from the distorted PPG signal by using the exponentially weighted moving average filter and to restore the final PPG AC signal from the primarily restored PPG AC signal through block interleaving.

According to various embodiments, the method of the computer device 100 further includes a step (step 810) of obtaining, by the initial unit 230, a basic period of a PPG signal from the PPG sensor 111 in an initial state, a step (step 820) of obtaining, by the update unit 240, a waveform and period of a PPG signal not having distortion from the PPG sensor 111 in the state in which motion artifacts are not present, and a step (step 850) of outputting, by the command unit 260, the final PPG AC signal.

According to various embodiments, the step of restoring the final PPG AC signal includes a step (step 840) of detecting, by the compensation unit 250, the final PPG AC signal by restoring a waveform of the distorted PPG signal.

According to various embodiments, the step (step 840) of detecting the final PPG AC signal includes a step of detecting, by the update unit 240, a DC gain change trend of the distorted PPG signal and a step of obtaining, by the compensation unit 250, the primarily restored PPG AC signal from a difference between the distorted PPG signal and the DC gain change trend by using the exponentially weighted moving average filter.

According to various embodiments, the step (step 840) of detecting the final PPG AC signal further includes a step of detecting, by the compensation unit 250, the final PPG AC signal from the primarily restored PPG signal and the PPG signal not having distortion through the block interleaving and a step of providing, by the compensation unit 250, the final PPG AC signal to the command unit.

According to various embodiments, the update unit 240 includes the PPG period measuring unit 447 configured to obtain the waveform and period of the PPG signal not having distortion from the PPG sensor 111, and the PPG distortion inspection unit 449 configured to inspect whether the PPG signal from the PPG sensor 111 has been distorted and to stop the PPG period measuring unit 447 and operate the compensation unit 250 when the distortion is detected.

According to various embodiments, the step (step 840) of detecting the final PPG AC signal is performed when the distortion is detected (step 830).

According to various embodiments, the method of the computer device 100 further includes a step of providing, by the update unit 240, the command unit 260 with the PPG signal not having distortion when the distortion is not detected and a step (step 850) of outputting, by the command unit 260, the PPG signal not having distortion.

According to various embodiments, the method of the computer device 100 is an implemented in an FPGA. The initial unit 230, the update unit 240, the compensation unit 250, and the command unit 260 are implemented in the form of a code installable in the FPGA.

The aforementioned method may be provided as a computer program recorded on a computer-readable recording medium in order to be executed in a computer. The medium may continue to store a program executable by a computer or may temporarily store the program for execution or download. Furthermore, the medium may be various recording means or storage means having a form in which one or a plurality of pieces of hardware has been combined. The medium is not limited to a medium directly connected to a computer system, but may be one distributed over a network. Examples of the medium may be magnetic media such as a hard disk, a floppy disk and a magnetic tape, optical media such as a CD-ROM and a DVD, magneto-optical media such as a floptical disk, and media configured to store program instructions, including, a ROM, a RAM, and a flash memory. Furthermore, other examples of the medium may include recording media and/or storage media managed in an app store in which apps are distributed, a site in which various other pieces of software are supplied or distributed, a server, etc.

The methods, operations or schemes of this disclosure may be implemented by various means. For example, such schemes may be implemented as hardware, firmware, software, or a combination of them. Those skilled in the art will understand that various exemplary logical blocks, modules, circuits, and algorithm steps described in association with the present disclosure may be implemented as electronic hardware, computer software, or combinations of them. In order to clearly describe such a mutual substitution of hardware and software, various exemplary components, blocks, modules, circuits, and steps have been generally described above from their functional viewpoints. Whether such a function is implemented as hardware or implemented as software is different depending on design requirements assigned to a specific application and the entire system. Those skilled in the art may implement a function described in various manners for each specific application, but such implementations should not be construed as departing from the scope of this disclosure.

In a hardware implementation, processing units used to perform schemes may be implemented within one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform functions described in this disclosure, a computer, or a combination of them.

Accordingly, various exemplary logical blocks, modules, and circuits described in association with this disclosure may be implemented or performed as a general-purpose processor, a DSP, an ASIC, an FPGA or another programmable logical device, a discrete gate or transistor logic, discrete hardware components or a given combination of them designed to perform functions described in the present disclosure. The general-purpose processor may be a microprocessor, but alternatively, the processor may be a given conventional processor, controller, microcontroller, or state machine. Furthermore, the processor may be implemented as a combination of computing devices, for example, a DSP and a microprocessor, a plurality of microprocessors, one or more microprocessors associated with a DSP core, or a combination of given other components.

In firmware and/or software implementation, schemes may be implemented as instructions stored in a computer-readable medium, such as a random access memory (RAM), a read-only memory (ROM), a non-volatile random access memory (NVRAM), a programmable read-only memory (PROM), an erasable programmable read-only memory (EPROM), an electrically erasable PROM (EEPROM), a flash memory, a compact disc (CD), a magnetic or optical data storage device. The instructions may be executed by one or more processors and may enable a processor(s) to perform specific aspects of a function described in this disclosure.

The aforementioned embodiments have been described as using aspects of the subject matter now disclosed in one or more independent computer systems, but this disclosure is not limited thereto and may be implemented in association with a network or a given computing environment, such as a distributed computing environment. Furthermore, in this disclosure, aspects of the subject matter may be implemented in a plurality of processing chips or devices, and storage may be similarly influenced in a plurality of devices. Such devices may include PCs, network servers, and portable devices.

Although this disclosure has been described in relation to some embodiments, the disclosure may be modified and changed in various ways without departing from the scope of this disclosure which may be understood by those skilled in the art to which an invention of this disclosure belongs. Furthermore, such a modification and change should be considered as belonging to the scope of the claims appended in the specification.

The invention claimed is:

1. A computer device comprising:
   a photoplethysmography (PPG) sensor configured to measure PPG; and
   a processor connected to the PPG sensor and configured to restore a final PPG AC signal by compensating for motion artifacts of a distorted PPG signal from the PPG sensor,
   wherein the processor is configured to:
      obtain a primarily restored PPG AC signal of two or more primarily restored PPG AC signals from the distorted PPG signal by using an exponentially weighted moving average filter,
      calculate the difference between the distorted PPG signal and a DC gain change trend signal of the distorted PPG signal to determine an AC gain change trend signal,
      calculate the ratio of the DC gain change trend signal and the AC gain change trend signal, and
      restore the final PPG AC signal from the primarily restored PPG AC signal and a previous PPG signal not having distortion through block interleaving, and
      wherein the block interleaving utilizes an average of the two or more primarily restored PPG AC signals to provide the final PPG AC signal.

2. The computer device of claim 1, wherein the processor comprises:
   an initial unit configured to obtain a basic period of a PPG signal from the PPG sensor in an initial state;
   an update unit configured to obtain a waveform and period of a PPG signal not having distortion from the PPG sensor in a state in which motion artifacts are not present;
   a compensation unit configured to detect the final PPG AC signal by restoring a waveform of the distorted PPG signal; and
   a command unit configured to output the final PPG AC signal.

3. The computer device of claim 2, wherein:
   the update unit is configured to detect a DC gain change trend of the distorted PPG signal, and
   the compensation unit is configured to obtain the primarily restored PPG AC signal from a difference between the distorted PPG signal and the DC gain change trend by using the exponentially weighted moving average filter.

4. The computer device of claim 3, wherein the compensation unit is configured to:
   detect the final PPG AC signal from the primarily restored PPG signal and the PPG signal not having distortion through the block interleaving, and
   provide the final PPG AC signal to the command unit.

5. The computer device of claim 2, wherein the update unit comprises:
   a PPG period measuring unit configured to obtain the waveform and period of the PPG signal not having distortion from the PPG sensor; and
   a PPG distortion inspection unit configured to inspect whether the PPG signal from the PPG sensor has been distorted and to stop the PPG period measuring unit and operate the compensation unit when the distortion is detected.

6. The computer device of claim 5, wherein the update unit is configured to provide the command unit with the PPG signal not having distortion when the distortion is not detected.

7. The computer device of claim 6, wherein the command unit is configured to output the PPG signal not having distortion.

8. The computer device of claim 2, wherein:
   the processor comprises a field programmable gate array (FPGA), and
   the initial unit, the update unit, the compensation unit, and the command unit are implemented in a form of a code installable in the FPGA.

9. A method of attenuating motion artifacts in photoplethysmography (PPG), comprising:
   measuring a change in a blood volume of a microvessel of a tissue with a PPG sensor to produce a PPG signal;
   receiving the PPG signal from the PPG sensor;
   determining if the PPG signal is distorted, and
   when the PPG signal is a distorted PPG signal, restoring a final PPG AC signal by compensating for motion artifacts of the distorted PPG signal,
   wherein the restoring of the final PPG AC signal comprises:
      obtaining a primarily restored PPG AC signal of two or more primarily restored PPG AC signals from the distorted PPG signal by using an exponentially weighted moving average filter;
      calculating the difference between the distorted PPG signal and a DC gain change trend signal of the distorted PPG signal to determine an AC gain change trend signal;
      calculating the ratio of the DC gain change trend signal and the AC gain change trend signal; and
      restoring the final PPG AC signal from the primarily restored PPG AC signal and a previous PPG signal not having distortion through block interleaving, and
      wherein the block interleaving utilizes an average of the two or more primarily restored PPG AC signals to provide the final PPG AC signal.

10. The method of claim 9, further comprising:
    obtaining, by an initial unit, a basic period of a PPG signal from the PPG sensor in an initial state;
    obtaining, by an update unit, a waveform and period of a PPG signal not having distortion from the PPG sensor in a state in which motion artifacts are not present; and
    outputting, by a command unit, the final PPG AC signal.

11. The method of claim 10, wherein the restoring of the final PPG AC signal comprises detecting, by a compensation unit, the final PPG AC signal by restoring a waveform of the distorted PPG signal.

12. The method of claim 11, wherein the detecting of the final PPG AC signal comprises:
  detecting, by the update unit, a DC gain change trend of the distorted PPG signal; and
  obtaining, by the compensation unit, the primarily restored PPG AC signal from a difference between the distorted PPG signal and the DC gain change trend by using the exponentially weighted moving average filter.

13. The method of claim 12, wherein the detecting of the final PPG AC signal further comprises:
  detecting, by the compensation unit, the final PPG AC signal from the primarily restored PPG signal and the PPG signal not having distortion through the block interleaving; and
  providing, by the compensation unit, the final PPG AC signal to the command unit.

14. The method of claim 10, wherein the update unit comprises:
  a PPG period measuring unit configured to obtain the waveform and period of the PPG signal not having distortion from the PPG sensor; and
  a PPG distortion inspection unit configured to inspect whether the PPG signal from the PPG sensor has been distorted and to stop the PPG period measuring unit and operate the compensation unit when the distortion is detected, and
  wherein the detecting of the final PPG AC signal is performed when the distortion is detected.

15. The method of claim 14, further comprising:
  providing, by the update unit, the command unit with the PPG signal not having distortion when the distortion is not detected; and
  outputting, by the command unit, the PPG signal not having distortion.

16. The method of claim 10, wherein the method is implemented in an FPGA, and
  wherein the initial unit, the update unit, the compensation unit, and the command unit are implemented in a form of a code installable in the FPGA.

\* \* \* \* \*